United States Patent [19]

Darby

[11] Patent Number: 4,677,767

[45] Date of Patent: Jul. 7, 1987

[54] SHOCK ABSORBING SURGICAL SHOE

[76] Inventor: H. Darrell Darby, 1038 Sixth Ave., Huntington, W. Va. 25701

[21] Appl. No.: 850,832

[22] Filed: Apr. 11, 1986

Related U.S. Application Data

[63] Continuation-in-part of Ser. No. 640,392, Aug. 13, 1984, abandoned.

[51] Int. Cl.[4] .................. A43B 11/00; A43B 13/18
[52] U.S. Cl. ...................................... 36/102; 36/110; 36/11.5; 36/45
[58] Field of Search .................. 36/88, 92, 102, 93, 36/103, 106, 104, 110, 107, 50, 83, 72 R, 138, 30 R, 45, 47, 55, 58.5, 97, 11.5; 12/142 N; 128/595, 581, 83.5

[56] References Cited

U.S. PATENT DOCUMENTS

| | | | |
|---|---|---|---|
| 2,742,717 | 4/1956 | Murray | 12/142 N |
| 3,333,353 | 8/1967 | Garcia | 36/68 |
| 3,566,487 | 3/1971 | Beightol | 36/110 |
| 3,661,151 | 5/1972 | Schoenbrun et al. | 128/87 R |
| 4,079,527 | 3/1978 | Antonious | 36/50 X |
| 4,133,118 | 1/1979 | Khalsa et al. | 36/83 |
| 4,300,294 | 11/1981 | Riecken | 36/97 |
| 4,370,818 | 2/1983 | Simoglou | 36/110 X |
| 4,463,761 | 8/1984 | Pols et al. | 36/88 X |
| 4,567,678 | 2/1986 | Morgan et al. | 36/110 |

Primary Examiner—Stephen Marcus
Assistant Examiner—T. Graveline
Attorney, Agent, or Firm—Peter L. Klempay

[57] ABSTRACT

A shoe of use on a post-operative or otherwise traumatized foot includes a sole assembly having a outer sole, a shock absorbing midsole and an inner sole conforming generally to the contour of the sole of the foot, the sole assembly having a limited degree of flexibility, and an upper assembly including an outer wall of a flexible mesh material and a lining of a soft, conformable material, adjustable straps connecting the opposite sides of the forward portion of the upper assembly. Preferably, the sole assembly is tapered, being of greatest thickness in the heel region; the heel portion of the upper is angled forwardly and upwardly; and one of the forward portions of the upper is of greater length than the other to protectively cover the dorsal aspect of the foot.

5 Claims, 6 Drawing Figures

SHOCK ABSORBING SURGICAL SHOE

This application is a continuation-in-part of application Ser. No. 640,392, filed on Aug. 13, 1984 and entitled SHOCK ABSORBING SURGICAL SHOE now abandoned.

The present invention pertains to post-operative surgical shoes and, more particularly, to such shoes which are capable of being adjustably contoured for cradling the bone structure of the foot and which provide improved support for the foot during healing.

BACKGROUND OF THE INVENTION

Following surgury or injury involving the bones of the foot, traditional practice has been to employ a rigid plaster-of-paris cast to support the foot while healing occurs. Recently, surgical shoes have been used in place of the rigid cast as such shoes are less encumbering and promote early ambulation. U.S. Pat. No. 3,661,151, Schoenbrun et al, discloses a surgical shoe of this type, the shoe having a composite sole including a flat, rigid plywood midsole, an outer sole and a thin foam rubber cushion innersole and an open-toed cloth upper.

The intended function of the plywood midsole is to provide rigidity for restraint of movement of the foot in the shoe during walking. However, during the propulsive phase of gait toe-off, the body weight, being imposed in the forward portion of the sole, forces the rigid sole away from the foot. This action, in which the heel pulls away from the sole, creates stress throughout the foot. Additionally, a rigid sole portion serves as a shock transmitter, to the discomfort of the wearer.

It is the primary object of the present invention to provide a surgical shoe having improved bone support and shock absorbing properties.

It is also an object of the present invention to provide such a shoe which may be contoured around the foot for improved support.

Another object of the invention is the provision of a surgical shoe which provides adjustable compression to reduce post-operative or post injury edema and pain and which permits motion in the joints to be maintained while avoiding or removing abnormal stresses from the bones of the foot.

SUMMARY OF THE INVENTION

The above and other objects of the invention which will become apparent hereinafter are achieved by the provision of a surgical shoe having a molded sole similar to those of conventional running shoes; an inner sole of an impressionable foam material to conform to the contours of the plantar aspects of the foot; an upper open in the toe region and having overlapping dorsal portions, the upper consisting of an outer layer of nylon mesh and an inner, soft layer; and closure straps preferrably of interlocking hook and loop material such as VELCRO overlying the dorsal portions. An insert of fiberglass casting material may be employed on the plantar aspect of the foot to provide additional rigidity and contouring when desired.

For a more complete understanding of the invention and the objects and advantages thereof, reference should be had to the following detailed description and the accompanying drawing wherein a preferred embodiment of the invention is described and illustrated.

DESCRIPTION OF THE PREFERRED EMBODIMENT

Figure 1:
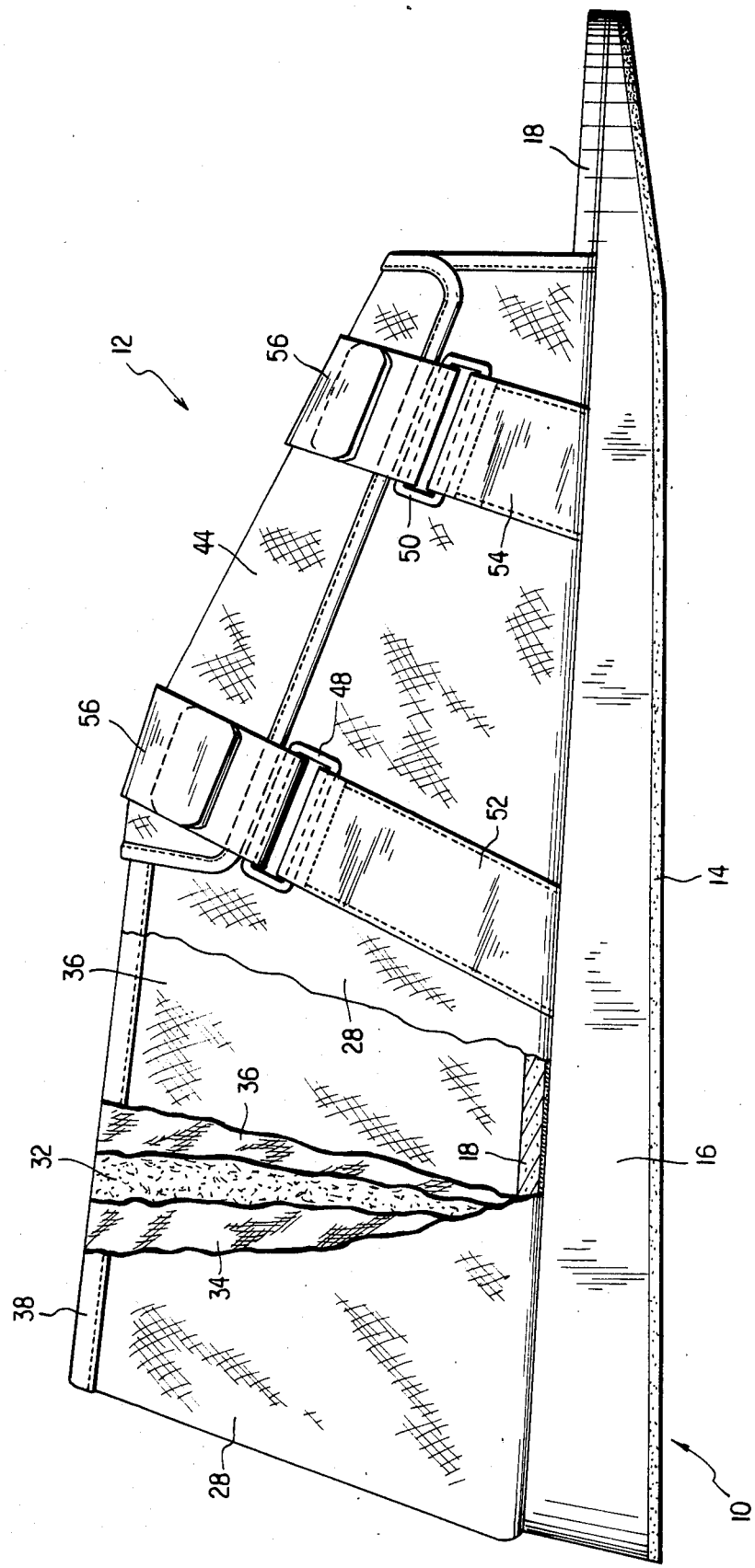
FIG. 1 is a side elevational view of the surgical shoe of the present invention, a portion thereof being broken away to illustrate the interior structure.
Figure 2:
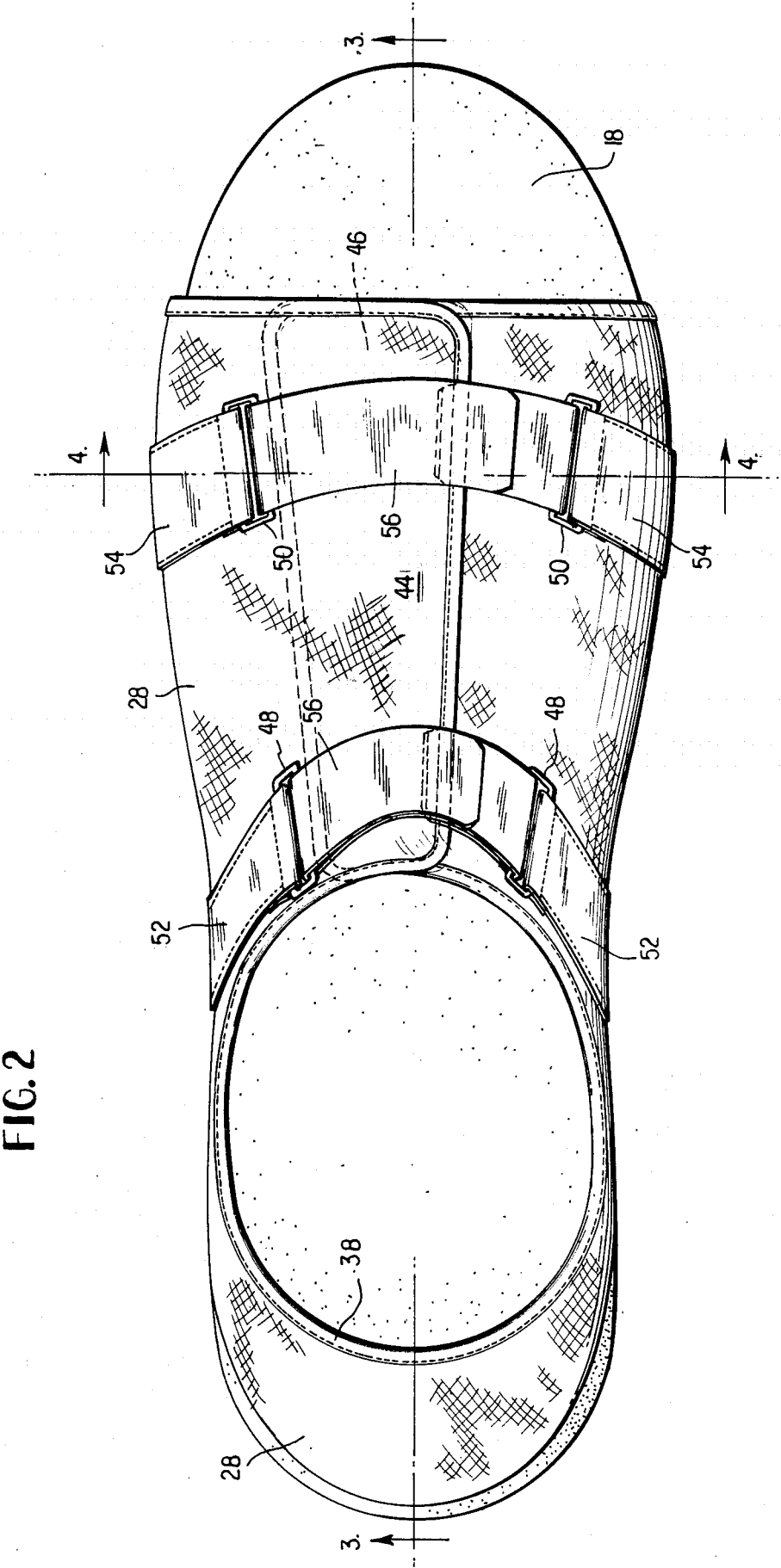
FIG. 2 is a top plan view of the surgical shoe.
Figure 3:
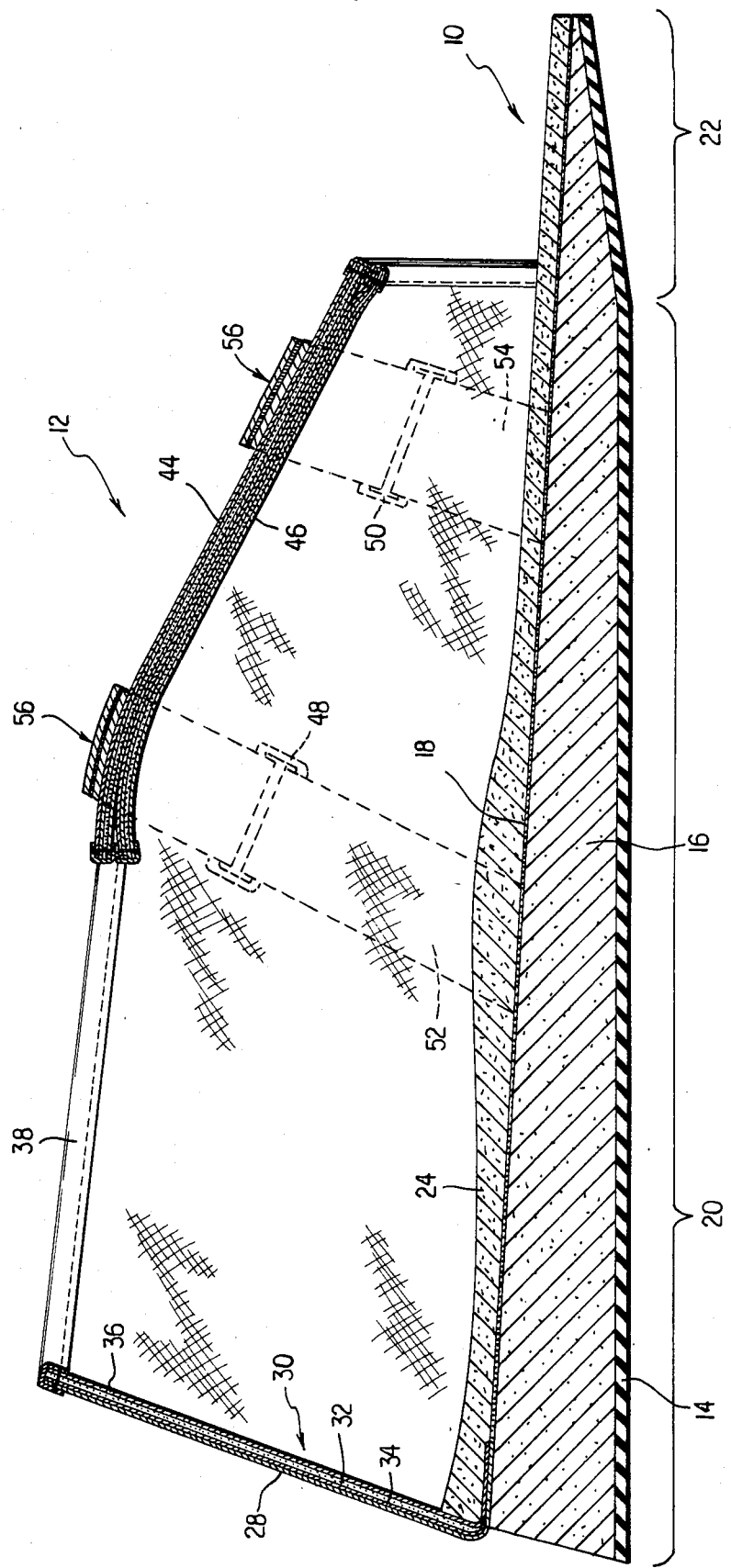
FIG. 3 is a longitudinal cross-sectional view taken on the line 3—3 of FIG. 2.
Figure 4:
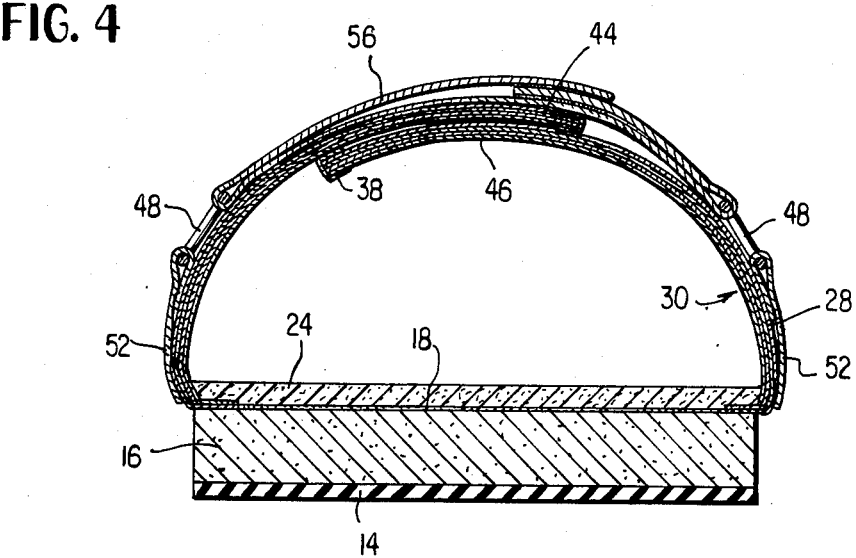
FIG. 4 is a transverse cross-sectional view taken on the line 4—4 of FIG. 2.

The surgical shoe of the present invention includes a sole assembly, designated generally by the reference numeral 10, and an upper assembly, designated generally by the numeral 12. The sole assembly includes an outer sole 14 of a wear resistant material such as rubber or similar plastic material and has a non-slip bottom surface with a tread or crepe pattern. Bonded to the outer sole 14 is a midsole 16 formed of a resilient, flexible material, preferably, ethylene-vinyl, acetate copolymer. As can be seen from FIGS. 1 and 3, the upper surface 18 of the midsole is planar and the lower surface is planar over the principal portion 20 thereof extending rearwardly from approximately a line underlying the metatarsal-phalange joints of the foot and over the forward portion 22 extending forwardly from this line, the forward portion being angled upwardly relative to the principal portion by a small acute angle. The midsole is of greatest thickness at the rear or heel region and tapers toward the front or toe region. By way of example, the thickness of the midsole at the heel region may be 2.3 cm, at the forward end of the principal portion, 1.5 cm, and, at the front end of the midsole, 0.5 cm. Overlying and bonded to the midsole 16 is an inner sole 24 of a foamed plastic material capable of molding or conforming to the plantar surface of the foot. The sole assembly 10, as can be seen from FIG. 2, is symmetrical with respect to the vertical plane passing through the longitudinal axis thereof.

The upper assembly 12 is secured to the midsole 16 by conventional techniques, preferably, by adhesive bonding. The upper assembly has an outer wall 28 of a substantially elastic, flexible material such as NYLON mesh and a lining 30 of a soft, conformable material, for example, a plastic foam 32 laminated between two layers 34, 36 of a shear woven fabric mesh, the lining being bonded to the inner face of the outer wall. The upper assembly extends along the heel and sides of the shoe, the toe region being open and the conventional shoe tongue being omitted. A trim strip 38 is secured, as by sewing, along the edges of the upper.

The forward portion of the upper 12 is formed with left and right flaps 44, 46, respectively, with one of the flaps, for example the left flap 44, being of greater length than the other. On the outer face of each of the flaps two elongated rings 48, 50 are provided, the rings being retained by straps 52, 54 of flexible but nonelastic material such as leather sewn to the corresponding flap, both straps being angled downwardly and rearwardly and the forward one thereof being shorter than the rear.

Figure 5:
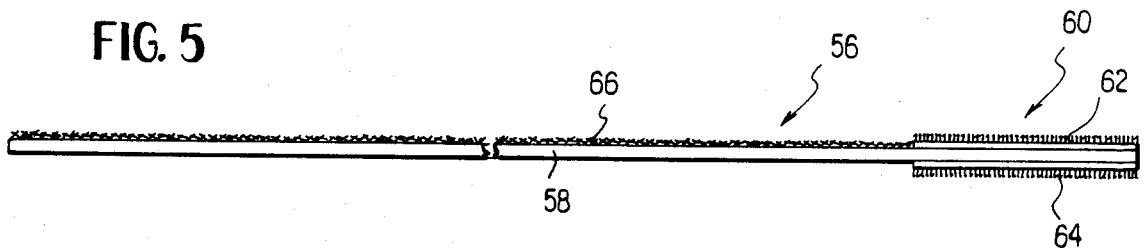
FIG. 5 is a side elevational view of one of the closure straps, detached from the shoe and on an enlarged scale relative to FIGS. 1-4.

The forward and rearward rings, respectively, on the two flaps are aligned transversely with one another. A closure strap 56 is provided for each pair of rings. Referring to FIG. 5, each closure strap consists of a cloth tape 58 having a first end portion 60 extending approximately one-quarter the length of the strip and covered on each face with a fabric layer 62, 64, respectively, having projecting hook-like elements. One face of the remainder of the closure strap is covered with loop-like elements 66. These hook and loop elements are of the type identified by the VELCRO trademark, for example. The closure strap is threaded through one of the elongated rings, for example the ring 48, on one flap of the shoe with the end portion 60 located below the ring and the loop-like element face directed outwardly, the strap being passed through the ring to the juncture of the end portion 60 and the remainder of the strap. At this point, the end portion 60 is folded over so that the hook-like element layer 62 engages the loop-like elements of the adjacent portion of the strap thereby retaining the strap on the corresponding ring. In order to close the shoe on a foot, the free end of the strap is passed through the corresponding ring on the opposite flap and doubled back to place the free end in engagement with the fastening element layer 64.

Completing the description of the surgical shoe, it will be noted that the heel region of the upper is angled forwardly and upwardly, for example at an angle of approximately 15°.

In use of the surgical shoe described above, the shoe is positioned on the foot of the patient, the larger flap 44 folded over the dorsal portion of the foot to provide protection for incisions which may have been made in this region, the shorter flap 46 folded over the flap 44 and, as was described above, the free ends of the straps 56 being passed through the corresponding rings and doubled back on themselves to bring the mating fabric layers 64 and 66 into engagement. By selection of the degree of tightness to which the straps are drawn, the shoe is caused to adapt to the contours of the foot. As the walls of the upper are formed of a flexible material, the forces imposed by the closure straps 56 are transmitted to the sole of the shoe, causing the same to closely conform to the contours of the foot. Consequently, the shoe closely conforms to the shape of the foot and provides support therefor without imposing excessive pressure thereto. It will be appreciated that the sole assembly provides a high degree of impact or shock absorption to reduce trauma to the surgical area or injured portions of the foot. The compression produced by the upper assembly reduces post-operative or post injury edema and reduces pain thus promoting healing and early ambulation. Due to the absence of rigid structures in the shoe sole, motion is maintained in the joints of the foot during recovery.

The wedge configuration of the sole, the sole being of greater thickness in the heel region than the forward portion thereof, provides a sole which conforms to the declination angle of the metatarsals of the foot. This feature, in combination with the conformable foam innersole, serves to provide both support and shock absorption for the foot structure. The combination of the angled heel configuration of the upper and the limited flexibility of the sole assembly serves to reduce heel slide during walking, assuring that the sole maintains support for the foot at all times.

Figure 6:
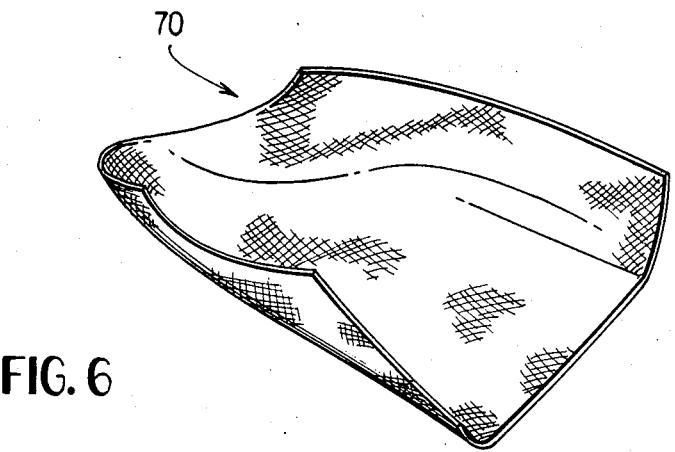
FIG. 6 is a perspective view of a molded insert which may be employed with the surgical shoe.

Where, due to the nature of the injury or surgury to the foot, additional support is required, an insert 70, such as is shown in FIG. 6, may be used in conjunction with the surgical shoe. Such an insert is formed of four to six layers of fiberglass casting material such as that sold by Johnson & Johnson, New Brunswick, N.J., under the trademark DELTA-LITE. Typically, the insert would be molded on the plantar aspect of the foot, extending from the heel to the metatarsal heads. The surgical shoe is then placed on the foot, the contouring and compression functions of the upper molding the fiberglass insert to the foot providing a rigid support in seven to ten minutes. The impact absorbing properties of the sole are maintained when using such an insert.

It will be understood that while a preferred embodiment of the invention has been shown and described, changes and additions may be made therein and thereto without departing from the spirit of the invention. Reference should, accordingly, be had to the appended claims in determining the true scope of the invention.

I claim:

1. A surgical shoe adapted for use on a post-operative or otherwise traumatized foot comprising:
  a sole assembly including an inner sole conforming generally to the plantar aspect of the foot, a midsole of an impact absorbing material, said midsole having its greatest thickness in the heel region and tapering downwardly toward the toe region, and an outer sole, said sole assembly having a degree of flexibility similar to that of a conventional running shoe sole assembly; and
  an upper assembly secured to said sole assembly and adapted to surround the heel, sides and dorsal portions of the foot while leaving the toe region open, the heel region of said upper assembly being angled forwardly and upwardly from the sole assembly, the forward portions of said upper assembly being divided into left and right flaps one of which is of greater length than the other, is adapted to cover the dorsal region of the foot, and underly said other of said flaps, and strap means for interconnecting the outerface portions of said left and right flaps.

2. The surgical shoe of claim 1 further including a molded fiberglass insert adapted to closely conform to the contour of a portion of the foot and to be interposed between the foot and said inner sole.

3. The surgical shoe of claim 1 wherein said upper assembly includes an outer wall of a woven nylon mesh material and a lining of a conformable plastic foam material.

4. The surgical shoe of claim 3 wherein said lining is bonded to the inner face of said outer wall.

5. The surgical shoe of claim 1 wherein said midsole is formed of ethylene-vinyl, acetate copolymer.

* * * * *